(12) United States Patent
Schilling et al.

(10) Patent No.: US 12,296,159 B2
(45) Date of Patent: May 13, 2025

(54) METHOD FOR PUMP START IN A FULLY IMPLANTED LVAD SYSTEM WHEN MULTIPLE POWER SOURCES MAY BE PRESENT

(71) Applicant: Boston Scientific Scimed, Inc., Maple Grove, MN (US)

(72) Inventors: Eric A. Schilling, Ham Lake, MN (US); Joel B. Artmann, Elk River, MN (US); Jason C. Lee, Edina, MN (US); David I. Siegfried, Edina, MN (US)

(73) Assignee: BOSTON SCIENTIFIC SCIMED, INC., Maple Grove, MN (US)

(*) Notice: Subject to any disclaimer, the term of this patent is extended or adjusted under 35 U.S.C. 154(b) by 1241 days.

(21) Appl. No.: 17/009,224

(22) Filed: Sep. 1, 2020

(65) Prior Publication Data
US 2022/0062514 A1  Mar. 3, 2022

(51) Int. Cl.
*A61M 60/50* (2021.01)
*A61M 60/40* (2021.01)
*A61M 60/871* (2021.01)

(52) U.S. Cl.
CPC ............ *A61M 60/50* (2021.01); *A61M 60/40* (2021.01); *A61M 60/871* (2021.01); *A61M 2205/3561* (2013.01); *A61M 2205/8206* (2013.01)

(58) Field of Classification Search
CPC .... A61M 60/50; A61M 60/871; A61M 60/40; A61M 2205/3561; A61M 2205/8206
See application file for complete search history.

(56) References Cited

U.S. PATENT DOCUMENTS

| 5,711,753 | A  | * | 1/1998  | Pacella ............... A61M 60/546 600/16 |
| 5,713,954 | A  |   | 2/1998  | Rosenberg et al. |
| 6,605,032 | B2 |   | 8/2003  | Benkowski et al. |
| 7,997,854 | B2 |   | 8/2011  | Larose et al. |
| 8,419,609 | B2 |   | 4/2013  | Shambaugh, Jr. et al. |
| 2003/0069465 | A1 |   | 4/2003  | Benkowski et al. |
| 2006/0247737 | A1 | * | 11/2006 | Olson ............... A61M 5/14276 607/33 |
| 2014/0275727 | A1 |   | 9/2014  | Bonde et al. |
| 2017/0185054 | A1 | * | 6/2017  | Rudser ................. G05B 13/021 |
| 2019/0374694 | A1 |   | 12/2019 | Farnan |

OTHER PUBLICATIONS

International Search Report and Written Opinion of International Application No. PCT/US2021/045295, dated Oct. 28, 2021, 13 pp.
Cardiopulminary Resuscitation in Adults and Children with Mechanical Circulatory Support: A Scientific from the American Heart Association. Circulation. Jun. 13, 2017, pp. e1115-e1134.

* cited by examiner

*Primary Examiner* — Lindsey G Wehrheim
(74) *Attorney, Agent, or Firm* — Seager Tufte & Wickhem, LLP

(57) ABSTRACT

A method of controlling operation of an implantable blood pump includes attempting to restart a stopped implantable blood pump for a predetermined number of attempts with either power from an internal battery of a controller in communication with the implantable blood pump or transcutaneous energy transfer system (TETS) power in communication with the internal battery and the implantable blood pump. Following the predetermined number of attempts, the method includes pausing attempting to restart the implantable blood pump and begin attempting to recharge the internal battery with TETS power.

20 Claims, 3 Drawing Sheets

METHOD FOR PUMP START IN A FULLY IMPLANTED LVAD SYSTEM WHEN MULTIPLE POWER SOURCES MAY BE PRESENT

CROSS-REFERENCE TO RELATED APPLICATION n/a.

FIELD

The present technology is generally related to implantable blood pumps, and in particular, a method and control circuit for starting a stopped pump.

BACKGROUND

There are various reasons as to why an implantable blood pump may be stopped. For example, there may be a clinician initiated stop or either power from an internal battery of the controller or transcutaneous energy transfer system (TETS) power is unavailable. In the case of a stopped pump, a pump restart command initiated by the controller may attempt to restart the pump. However, automatically restarting the pump after a prolonged period of time may be undesirable due to thrombus formation within the pump or within the heart, for example.

SUMMARY

The techniques of this disclosure generally relate to implantable blood pumps, and in particular, a method and control circuit for starting a stopped pump.

In one aspect, the present disclosure provides a method of controlling operation of an implantable blood pump. The method includes attempting to restart a stopped implantable blood pump for a predetermined number of attempts with either power from an internal battery of a controller in communication with the implantable blood pump or transcutaneous energy transfer system (TETS) power in communication with the internal battery and the implantable blood pump. Following the predetermined number of attempts, the method includes pausing attempting to restart the implantable blood pump and begin attempting to recharge the internal battery with TETS power.

In another aspect of this embodiment, the predetermined number of attempts is at least 10.

In another aspect of this embodiment, if internal battery power sufficient to attempt to restart the pump becomes available following the predetermined number of attempts, the method further includes attempting to restart the stopped implantable blood pump.

In another aspect of this embodiment, if a new power source becomes available following the predetermined number of attempts, the method further includes attempting to restart the stopped implantable blood pump with the new power source.

In another aspect of this embodiment, if within thirty minutes from a last of the predetermined number of attempts, internal battery power sufficient to attempt a start of the implantable blood pump become available, the method further including attempting to restart the implantable blood pump at least two more times with internal battery power.

In another aspect of this embodiment, if a clinician entered command to restart the pump is initiated following the last of the predetermined number of attempts, the method further including attempting to restart the implantable blood pump.

In another aspect of this embodiment, if internal battery power sufficient to restart the implantable blood pump becomes available during any of the predetermined number of attempts, the method further includes attempting to restart the implantable blood pump using internal battery power only.

In another aspect of this embodiment, the implantable blood pump is a ventricular assist device.

In another aspect of this embodiment, the controller is an implanted controller.

In one aspect, a control circuit for an implantable blood pump includes processing circuitry configured to attempt to restart a stopped implantable blood pump for a predetermined number of attempts with either power from an internal battery of a controller in communication with the implantable blood pump or transcutaneous energy transfer system (TETS) power in communication with the internal battery and the implantable blood pump and following the predetermined number of attempts, pause attempting to restart the implantable blood pump and begin attempting to recharge the internal battery with TETS power.

In another aspect of this embodiment, the predetermined number of attempts is at least 10.

In another aspect of this embodiment, if internal battery power sufficient to attempt to restart the pump becomes available following the predetermined number of attempts, the processing circuitry is further configured to attempt to restart the stopped implantable blood pump.

In another aspect of this embodiment, if a new power source becomes available following the predetermined number of attempts, the processing circuitry is further configured to restart the stopped implantable blood pump with the new power source.

In another aspect of this embodiment, if within a predetermined amount of time from a last of the predetermined number of attempts, internal battery power sufficient to attempt a start of the implantable blood pump become available, the processing circuitry is further configured to attempt to restart the implantable blood pump at least two more times with internal battery power.

In another aspect of this embodiment, if a clinician entered command to restart the pump is initiated following the last of the predetermined number of attempts, the processing circuitry is further configured to attempt to restart the implantable blood pump.

In another aspect of this embodiment, if internal battery power sufficient to restart the implantable blood pump becomes available during any of the predetermined number of attempts, the processing circuitry is further configured to attempt to restart the implantable blood pump using internal battery power only.

In another aspect of this embodiment, wherein the implantable blood pump is a ventricular assist device.

In another aspect of this embodiment, wherein the controller is an implanted controller.

In another aspect of this embodiment, wherein the predetermined number of attempts is more than two.

In one aspect, a control circuit for an implantable blood pump includes processing circuitry configured to attempt to restart a stopped implantable blood pump for ten attempts with either power from an internal battery of a controller in communication with the implantable blood pump or transcutaneous energy transfer system (TETS) power in communication with the internal battery and the implantable blood pump. Following the ten attempts, the control circuit is further configured to pause attempting to restart the implantable blood pump and begin attempting to recharge the internal battery with TETS power. If internal battery power sufficient to attempt to restart the pump becomes available following the ten attempts, the processing circuitry is further configured to attempt to restart the stopped implantable blood pump. If a new power source becomes available following the ten attempts, the processing circuitry is further configured to restart the stopped implantable blood pump with the new power source. If within thirty minutes from a last of the ten attempts, internal battery power sufficient to attempt a start of the implantable blood pump become available, the processing circuitry is further configured to attempt to restart the implantable blood pump at least two more times with internal battery power.

The details of one or more aspects of the disclosure are set forth in the accompanying drawings and the description below. Other features, objects, and advantages of the techniques described in this disclosure will be apparent from the description and drawings, and from the claims.

BRIEF DESCRIPTION OF THE DRAWINGS

A more complete understanding of the present invention, and the attendant advantages and features thereof, will be more readily understood by reference to the following detailed description when considered in conjunction with the accompanying drawings wherein.

DETAILED DESCRIPTION

It should be understood that various aspects disclosed herein may be combined in different combinations than the combinations specifically presented in the description and accompanying drawings. It should also be understood that, depending on the example, certain acts or events of any of the processes or methods described herein may be performed in a different sequence, may be added, merged, or left out altogether (e.g., all described acts or events may not be necessary to carry out the techniques). In addition, while certain aspects of this disclosure are described as being performed by a single module or unit for purposes of clarity, it should be understood that the techniques of this disclosure may be performed by a combination of units or modules associated with, for example, a medical device.

In one or more examples, the described techniques may be implemented in hardware, software, firmware, or any combination thereof. If implemented in software, the functions may be stored as one or more instructions or code on a computer-readable medium and executed by a hardware-based processing unit. Computer-readable media may include non-transitory computer-readable media, which corresponds to a tangible medium such as data storage media (e.g., RAM, ROM, EEPROM, flash memory, or any other medium that can be used to store desired program code in the form of instructions or data structures and that can be accessed by a computer).

Instructions may be executed by one or more processors, such as one or more digital signal processors (DSPs), general purpose microprocessors, application specific integrated circuits (ASICs), field programmable logic arrays (FPGAs), or other equivalent integrated or discrete logic circuitry. Accordingly, the term "processor" as used herein may refer to any of the foregoing structure or any other physical structure suitable for implementation of the described techniques. Also, the techniques could be fully implemented in one or more circuits or logic elements.

Figure 1:
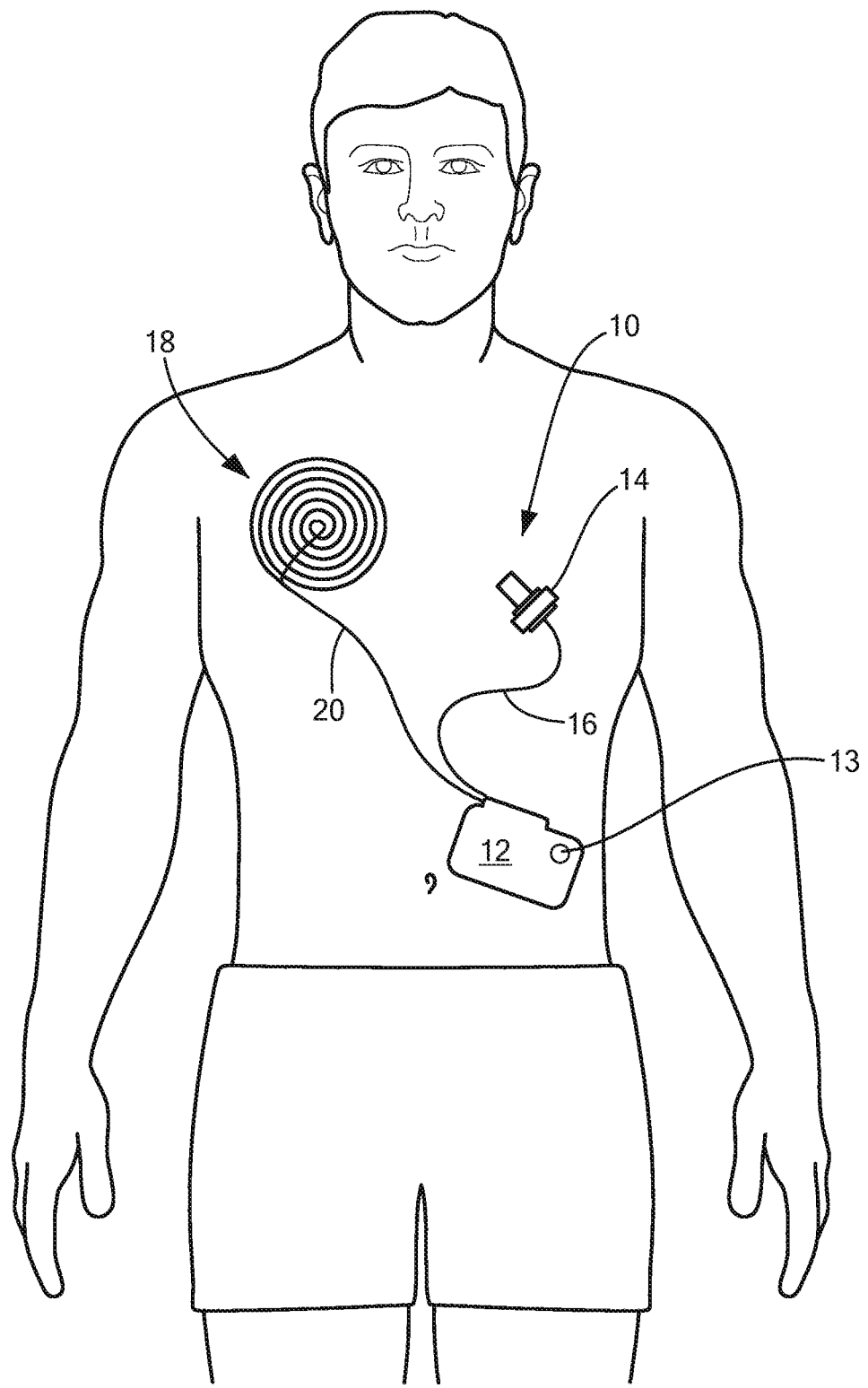
FIG. 1 is an internal system view of an implantable blood pump with a TETS receiver source constructed in accordance with the principles of the present application.
Figure 2:
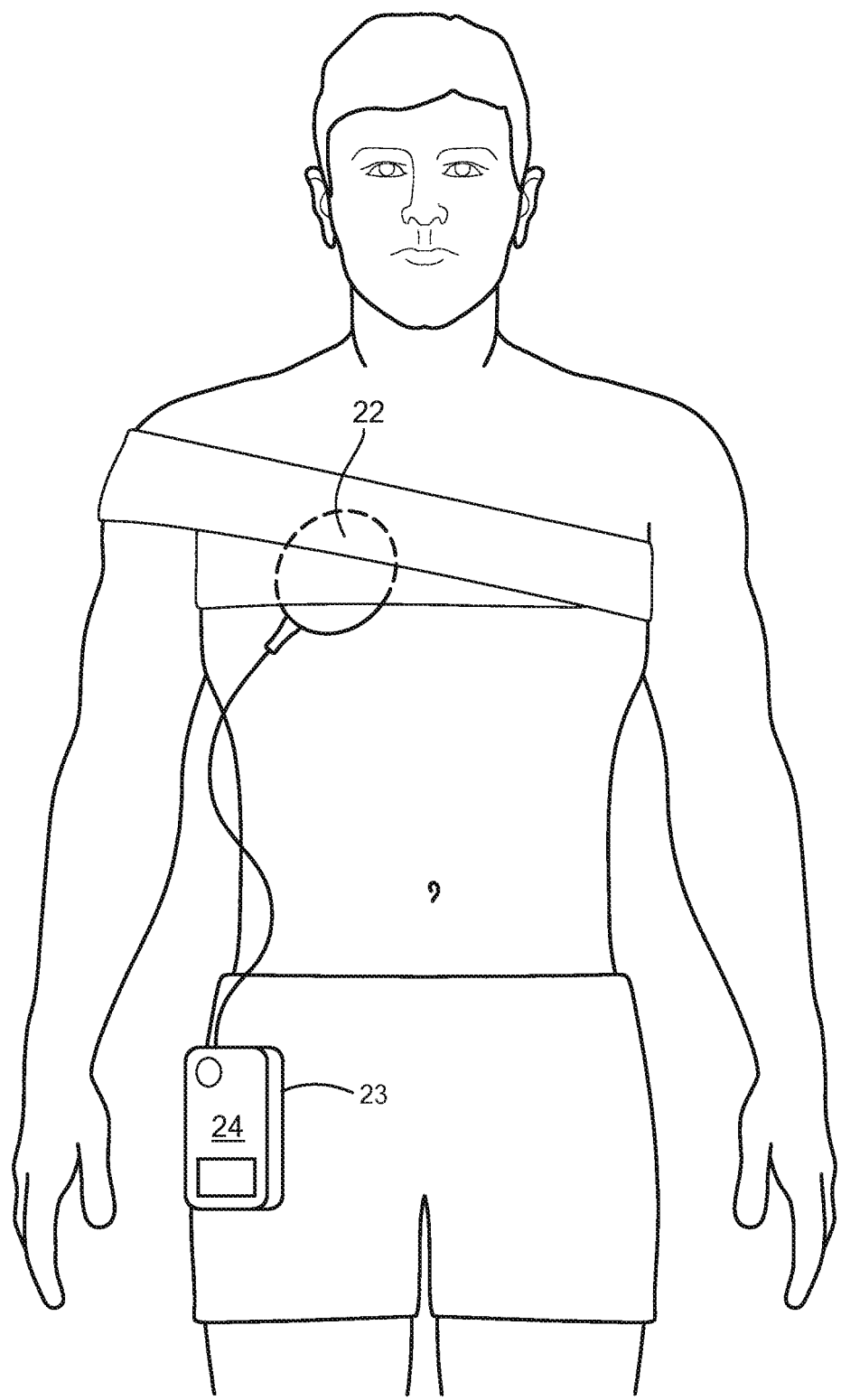
FIG. 2 is an external view of a TETS transmitter and a controller of the system shown in FIG. 1.

Referring now to the drawings in which like reference designators refer to like elements there is shown in FIGS. 1 and 2 an exemplary mechanical circulatory support device ("MCSD") constructed in accordance with the principles of the present application and designated generally as "10." The MCSD 10 may be fully implantable within a patient, whether human or animal, which is to say there are no percutaneous connections between the implanted components of the MCSD 10 and the components outside of the body of the patient. In the configuration shown in FIG. 1, the MCSD 10 includes an internal controller 12 implanted within the body of the patient. The internal controller 12 includes a control circuit having processing circuitry configured to control operation of an implantable blood pump 14. The internal controller 12 may include an internal power source 13, configured to power the components of the controller and provide power to one or more implantable medical devices, for example, the implantable blood pump, such as a ventricular assist device ("VAD") 14 implanted within the left ventricle of the patient's heart. The power source 13 may include a variety of different types of power sources including an implantable battery. VADs 14 may include centrifugal pumps, axial pumps, or other kinds electromagnetic pumps configured to pump blood from the heart to blood vessels to circulate around the body. One such centrifugal pump is the HVAD and is shown and described in U.S. Pat. No. 7,997,854, the entirety of which is incorporated by reference. One such axial pump is the MVAD and is shown and described in U.S. Pat. No. 8,419,609, the entirety of which is incorporated herein by reference. In an exemplary configuration, the VAD 14 is electrically coupled to the internal controller 12 by one or more implanted conductors 16 configured to provide power to the VAD 14, relay one or more measured feedback signals from the VAD 14, and/or provide operating instructions to the VAD 14.

Continuing to refer to FIG. 1, a receiving or internal coil 18 may also be coupled to the internal controller 12 by, for example, one or more implanted conductors 20. In an exemplary configuration, the receiving coil 18 may be implanted subcutaneously proximate the thoracic cavity, although any subcutaneous position may be utilized for implanting the receiving coil 18. The receiving coil 18 is configured to be inductively powered through the patient's skin by a transmission or external coil 22 (seen in FIG. 2) disposed opposite the receiving coil 18 on the outside/ exterior of the patient's body. For example, as shown in FIG. 2, a transmission coil 22 may be coupled to an external controller 23 having a power source 24, for example, a portable battery carried by the patient or wall power. In one configuration, the battery is configured to generate a radiofrequency signal for transmission of energy from the transmission coil 22 to the receiving coil 18. The receiving coil 18 may be configured for transcutaneous inductive communication with the transmission coil 22 to define a transcutaneous energy transfer system (TETS) that receives power from the transmission coil.

Figure 3:
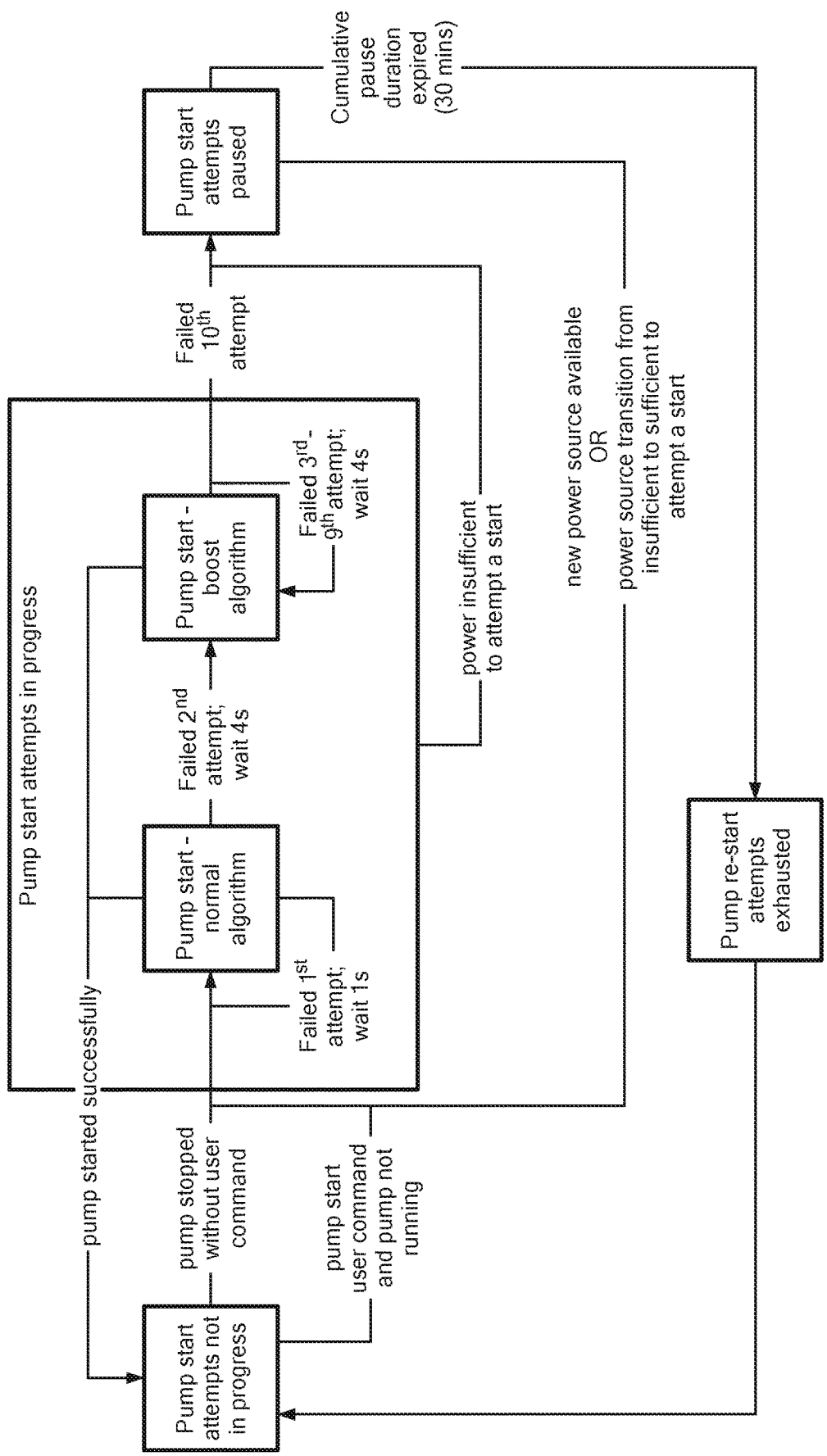
FIG. 3 is a flow chart showing a method of managing attempts to start a stopped pump.

Referring now to FIG. 3 in which a method of controlling operation of the implantable blood pump 14 is shown. In an exemplary configuration, the processing circuitry of controller 12 performs the various steps described herein. For example, if the pump 14 is stopped, but not by a command from a clinician, the processing circuitry is configured to attempt to restart the pump for a predetermined number of attempts. In one configuration, if the pump does not start after the first attempt, the controller 12 pauses for a predetermined amount of time, for example, between 0.5 second and 2.5 second before attempting a second time to restart the pump. If after the second attempt the pump 14 does not start, the processing circuitry is configured to pause for between 3.5 and 5.5 seconds before attempting a second attempt, and any additional attempts, to restart the pump 14. In an exemplary configuration, a total of 10 attempts to restart the pump 14 are attempted. If after the predetermined number of attempts to restart the pump 14 the pump does not start, no further attempts are made to restart the pump 14 and the processing circuitry is configured to attempt to recharge the internal battery 13 with TETS power. If following the predetermined number of attempts to restart the pump 14 the internal battery becomes charged sufficiently to attempt to restart the pump 14, the processing circuitry is configured to attempt to restart the implantable blood pump. Moreover, if a new power source becomes available after the predetermined number of attempts, for example, if a battery or wall power in communication with the TETS becomes available, then a restart attempt is made with the new power source. However, if within thirty minutes from a last of the predetermined number of attempts, internal battery power sufficient to attempt a start of the implantable blood pump 14 become available, the processing circuitry is further configured to attempt to restart the implantable blood pump 14 at least two more times with internal battery power. The thirty-minute time window prevents the pump from attempting to be started when thrombus or other heart clots may have accumulated. That is 30 minutes is the maximum amount of time a restart may be attempted without an override command initiated by the clinician. Moreover, if internal battery power sufficient to restart the implantable blood pump becomes available during any of the predetermined number of attempts, then the processing circuitry attempts to restart the implantable blood pump 14 using internal battery power only and not TETS power. This is so because the power level from the internal battery is typically greater than from TETS power.

It will be appreciated by persons skilled in the art that the present invention is not limited to what has been particularly shown and described herein above. In addition, unless mention was made above to the contrary, it should be noted that all of the accompanying drawings are not to scale. A variety of modifications and variations are possible in light of the above teachings without departing from the scope and spirit of the invention, which is limited only by the following claims.

What is claimed is:

1. A method of controlling operation of an implantable blood pump, comprising:
    attempting to restart a stopped implantable blood pump for a predetermined number of attempts with either power from an internal battery of a controller in communication with the implantable blood pump or transcutaneous energy transfer system (TETS) power in communication with the internal battery and the implantable blood pump; and
    following the predetermined number of attempts, pause attempting to restart the implantable blood pump and begin attempting to recharge the internal battery with TETS power.

2. The method of claim 1, wherein the predetermined number of attempts is at least 10.

3. The method of claim 1, further comprising attempting to restart the stopped implantable blood pump again based on an internal battery power sufficient to attempt to restart the pump becoming available following the predetermined number of attempts.

4. The method of claim 1, further comprising attempting to restart the stopped implantable blood pump again with a new power source based on the new power source becoming available following the predetermined number of attempts.

5. The method of claim 1, further comprising attempting to restart the stopped implantable blood pump again at least two more times with internal battery power based on, within a predetermined amount of time from a last of the predetermined number of attempts, an internal battery power sufficient to attempt a start of the implantable blood pump becoming available.

6. The method of claim 1, further comprising attempting to restart the stopped implantable blood pump again based on a clinician entered command to restart the pump being initiated following the last of the predetermined number of attempts.

7. The method of claim 1, further comprising attempting to restart the stopped implantable blood pump again using internal battery power only based on an internal battery power sufficient to restart the implantable blood pump becoming available during any of the predetermined number of attempts.

8. The method of claim 1, wherein the implantable blood pump is a ventricular assist device.

9. The method of claim 1, wherein the controller is an implanted controller.

10. A control circuit for an implantable blood pump, comprising:
    processing circuitry configured to:
        attempt to restart a stopped implantable blood pump for a predetermined number of attempts with either power from an internal battery of a controller in communication with the implantable blood pump or transcutaneous energy transfer system (TETS) power in communication with the internal battery and the implantable blood pump; and
        following the predetermined number of attempts, pause attempting to restart the implantable blood pump and begin attempting to recharge the internal battery with TETS power.

11. The control circuit of claim 10, wherein the predetermined number of attempts is at least 10.

12. The control circuit of claim 10, wherein the processing circuitry is further configured to attempt to restart the stopped implantable blood pump again based on an internal battery power sufficient to attempt to restart the pump becoming available following the predetermined number of attempts.

13. The control circuit of claim 10, wherein the processing circuitry is further configured to restart the stopped implantable blood pump again with a new power source based on the new power source becoming available following the predetermined number of attempts.

14. The control circuit of claim 10, wherein the processing circuitry is further configured to attempt to restart the implantable blood pump again at least two more times with internal battery power based on, within thirty minutes from a last of the predetermined number of attempts, an internal battery power sufficient to attempt a start of the implantable blood pump becoming available.

15. The control circuit of claim 10, wherein the processing circuitry is further configured to attempt to restart the implantable blood pump again based on a clinician entered command to restart the pump being initiated following the last of the predetermined number of attempts.

16. The control circuit of claim 10, wherein the processing circuitry is further configured to attempt to restart the implantable blood pump again using internal battery power only based on and internal battery power sufficient to restart the implantable blood pump becoming available during any of the predetermined number of attempts.

17. The control circuit of claim 10, wherein the implantable blood pump is a ventricular assist device.

18. The control circuit of claim 10, wherein the controller is an implanted controller.

19. The control circuit of claim 10, wherein the predetermined number of attempts is more than two.

20. A control circuit for an implantable blood pump, comprising:
processing circuitry configured to:
attempt to restart a stopped implantable blood pump for ten attempts with either power from an internal battery of a controller in communication with the implantable blood pump or transcutaneous energy transfer system (TETS) power in communication with the internal battery and the implantable blood pump;
following the ten attempts, pause attempting to restart the implantable blood pump and begin attempting to recharge the internal battery with TETS power;
attempt to restart the stopped implantable blood pump again based on an internal battery power sufficient to attempt to restart the pump becoming available following the ten attempts;
attempt to restart the stopped implantable blood pump again with a new power source based on the if a new power source becoming available following the ten attempts; and
attempt to restart the stopped implantable blood pump again at least two more times with internal battery power based on, within thirty minutes from a last of the ten attempts, an internal battery power sufficient to attempt a start of the implantable blood pump becoming available.

* * * * *